(12) United States Patent
Wang et al.

(10) Patent No.: US 11,513,088 B1
(45) Date of Patent: Nov. 29, 2022

(54) METHOD FOR COMPREHENSIVELY CHARACTERIZING LOWER LIMIT OF OIL ACCUMULATION OF DEEP MARINE CARBONATE RESERVOIR

(71) Applicant: INSTITUTE OF GEOLOGY AND GEOPHYSICS, CHINESE ACADEMY OF SCIENCES, Beijing (CN)

(72) Inventors: Wenyang Wang, Beijing (CN); Rixiang Zhu, Beijing (CN); Xiongqi Pang, Beijing (CN); Zhangxing Chen, Beijing (CN); Yaping Wang, Beijing (CN); Wang Zhang, Beijing (CN); Tao Hu, Beijing (CN)

(73) Assignee: INSTITUTE OF GEOLOGY AND GEOPHYSICS, CHINESE ACADEMY OF SCIENCES, Beijing (CN)

(*) Notice: Subject to any disclaimer, the term of this patent is extended or adjusted under 35 U.S.C. 154(b) by 0 days.

(21) Appl. No.: 17/681,941

(22) Filed: Feb. 28, 2022

(30) Foreign Application Priority Data

Nov. 5, 2021 (CN) .......................... 202111305786.4

(51) Int. Cl.
*G01N 24/08* (2006.01)
*G01N 33/24* (2006.01)

(52) U.S. Cl.
CPC ......... *G01N 24/081* (2013.01); *G01N 33/241* (2013.01)

(58) Field of Classification Search
CPC ............... G01N 24/081; G01N 33/241; G01N 15/0886; G01V 1/306; G01V 11/002; E21B 49/02; E21B 49/00; G06F 30/23
See application file for complete search history.

(56) References Cited

U.S. PATENT DOCUMENTS 10,161,891 B1  12/2018 Tian et al.
2007/0276639 A1*  11/2007 Montaron ............... G06F 30/23
                                                              703/10

(Continued)

FOREIGN PATENT DOCUMENTS

CN  103926632 A     7/2014
CN  105842750 A  *  8/2016  ............... G01V 9/00

(Continued)

OTHER PUBLICATIONS

Wei Xiaowei, et al., Methods of Determining The Matrix Petrophysical Cutoffs of Low Porosity and Low Permeability Sandstone Reservoir—Taking The J2s1 Oil Reservoir In La Field In Central Sichuan As An Example, Natural Gas Industry, 2005, pp. 28-31, vol. 25 Issue A.

(Continued)

*Primary Examiner* — Catherine T. Rastovski
*Assistant Examiner* — Kaleria Knox
(74) *Attorney, Agent, or Firm* — Bayramoglu Law Offices LLC

(57) ABSTRACT

A method, system and device for comprehensively characterizing a lower limit of oil accumulation of a deep marine carbonate reservoir is provided, aiming to solve the problem that the prior art cannot: accurately determine the lower limit of oil accumulation of the deep marine carbonate reservoir, which leads to the difficulty in predicting and identifying deep effective reservoirs. The method includes: determining lower limit porosity and permeability for oil accumulation based on a boundary line; determining lower limit porosity and permeability for oil accumulation based on a movable oil ratio of a core sample; determining a lower limit pore throat radius for oil accumulation based on a mercury injection experiment; and comprehensively characterizing the lower limit of oil accumulation of a deep marine car- (Continued)

bonate reservoir to be predicted. The method, system and device can predict and identify deep effective reservoirs.

13 Claims, 5 Drawing Sheets

(56) References Cited

U.S. PATENT DOCUMENTS

| | | | |
|---|---|---|---|
| 2012/0130639 A1* | 5/2012 | Hanson | E21B 49/00 |
| | | | 702/2 |
| 2016/0187532 A1* | 6/2016 | Hurley | G01V 11/002 |
| | | | 702/12 |
| 2018/0259467 A1* | 9/2018 | Buono | E21B 49/02 |
| 2019/0011584 A1* | 1/2019 | Qu | G01V 1/306 |
| 2020/0249216 A1* | 8/2020 | Tian | G01N 15/0886 |

FOREIGN PATENT DOCUMENTS

| | | | | |
|---|---|---|---|---|
| CN | 105842750 A | | 8/2016 | |
| CN | 107727679 A | | 2/2018 | |
| CN | 103926632 | * | 5/2018 | |
| CN | 108827999 | * | 11/2018 | G01N 24/081 |
| CN | 108827999 A | | 11/2018 | |

OTHER PUBLICATIONS

Song Mingshui, et al., Lower Limits of Physical Properties of Effective Carboniferous Igneous Reservoir In Su13 Well Block of West Junggar Basin, Journal of Geomechanics, 2019, pp. 1075-1081, vol. 25, No. 6.

\* cited by examiner

| Acquire historical data of a deep marine carbonate reservoir to be predicted, such as a burial depth, a porosity, a permeability and a fluid encountered during drilling; construct a first cross plot and a second cross plot; obtain a boundary line between the dry layer and the oil layer; and determine lower limit porosity and permeability for oil accumulation based on the boundary line as a first porosity and a first permeability, respectively | — S100 |

↓

| Collect a set number of core samples within a set porosity range, and measure a porosity, a permeability and an oil saturation of each of the core samples; subject the core samples to a water-oil displacement NMR experiment; obtain a movable oil ratio according to a change in the oil saturation of each of the core samples during the water-oil displacement NMR experiment; and determine lower limit porosity and permeability for oil accumulation based on the movable oil ratio as a second porosity and a second permeability, respectively | — S200 |

↓

| Perform a mercury injection experiment; calculate, based on parameters acquired by the mercury injection experiment, permeability contributions of different flow pore throat radii by a Purcell formula, and accumulate to obtain a cumulative permeability contribution; determine minimum flow pore throat radii corresponding to each of the core samples according to the cumulative permeability contribution; and determine a smallest one among the minimum flow pore throat radii as a lower limit flow pore throat radius for oil accumulation | — S300 |

↓

| Comprehensively characterize a lower limit of oil accumulation of the deep marine carbonate reservoir according to the first porosity, the first permeability, the second porosity, the second permeability and the lower limit flow pore throat radius for oil accumulation | — S400 |

FIG. 1

Statistical characterization module
100

Experimental characterization module
200

Statistical and experimental characterization module
300

Comprehensive characterization module
400

FIG. 2

METHOD FOR COMPREHENSIVELY CHARACTERIZING LOWER LIMIT OF OIL ACCUMULATION OF DEEP MARINE CARBONATE RESERVOIR

CROSS REFERENCE TO THE RELATED APPLICATIONS

This application is based upon and claims priority to Chinese Patent Application No. 202111305786.4, filed on Nov. 5, 2021, the entire contents of which are incorporated herein by reference.

TECHNICAL FIELD

The present invention belongs to the technical field of oil and gas exploration, and in particular relates to a method for comprehensively characterizing the lower limit of oil accumulation of a deep marine carbonate reservoir.

BACKGROUND

The lower limit of oil accumulation signifies the end of oil accumulation due to the loss of free space for holding fluid in reservoirs in petroliferous basins, and can generally be expressed comprehensively by porosity, permeability or pore throat radius. Above the lower limit, the geological conditions are favorable for the formation and distribution of reservoirs and the development of oil exploration. Under the lower limit, the geological conditions are not conducive to the formation and distribution of reservoirs, and there is a high risk to oil exploration. At present, it is hard to find new oil and gas reserves in the middle and shallow layers of petroliferous basins less than 4,500 m. Oil and gas exploration continues to move towards the deep layers of petroliferous basins, and the development of deep oil and gas resources has become an inevitable trend. In China, as the number of deep wells and the drilling depth increase year by year, more and more reservoirs are discovered in the deep marine carbonate succession, and the burial depth of the reservoirs is increasing, with the deepest industrial reservoir reaching more than 8,200 m. The deep marine carbonate reservoir has become an emerging exploration field. The geological conditions differ a lot in deep and shallow layers. Oil can accumulate in deep layers that are tighter than shallow layers, but the standard of shallow layers is not suitable to evaluate deep effective reservoirs. The definition and determination of the lower limit of oil accumulation of a deep marine carbonate reservoir is a problem that oil explorers are concerned about. The study of the lower limit of oil accumulation of the deep marine carbonate reservoir is of great significance for predicting effective reservoirs at deep marine strata and scientifically guiding deep oil drilling. Based on this, the present invention proposes a method for comprehensively characterizing the lower limit of oil accumulation of the deep marine carbonate reservoir.

SUMMARY

In order to solve the problem that the prior art cannot accurately determine a lower limit of oil accumulation of a deep marine carbonate reservoir, which leads to the difficulty in predicting and identifying deep effective reservoirs, the present invention proposes a method for comprehensively characterizing the lower limit of oil accumulation of the deep marine carbonate reservoir, aiming to predict the lower limit of oil accumulation of the deep marine carbonate reservoir, including the following steps:

S100: acquiring historical data of a deep marine carbonate reservoir to be predicted, such as a burial depth, a porosity, a permeability and a fluid encountered during drilling, where the encountered fluid includes an oil layer and a dry layer; constructing a first cross plot and a second cross plot; obtaining a boundary line between the dry layer and the oil layer; and determining lower limit porosity and permeability for oil accumulation based on the boundary line as a first porosity and a first permeability, respectively, where the first cross plot is a cross plot of the encountered fluid, the burial depth and the porosity; and the second cross plot is a cross plot of the encountered fluid, the burial depth and the permeability;

S200: collecting a set number of core samples within a set porosity range from the deep marine carbonate reservoir to be predicted, and measuring a porosity, a permeability and an oil saturation of each of the core samples by a nuclear magnetic resonance (NMR) instrument; subjecting the core samples to a water-oil displacement NMR experiment; obtaining a movable oil ratio according to a change in the oil saturation of each of the core samples during the water-oil displacement NMR experiment; and determining lower limit porosity and permeability for oil accumulation based on the movable oil ratio as a second porosity and a second permeability, respectively;

S300: collecting core samples again from the deep marine carbonate reservoir to be predicted, and performing a mercury injection experiment; calculating, based on parameters acquired by the mercury injection experiment, permeability contributions of different flow pore throat radii by a Purcell formula, and accumulating to obtain a cumulative permeability contribution; determining minimum flow pore throat radii corresponding to each of the core samples according to the cumulative permeability contribution; and determining a smallest one among the minimum flow pore throat radii as a lower limit flow pore throat radius for oil accumulation, where the parameters acquired by the mercury injection experiment include a mercury injection increment, a flow pore throat radius, a J function value and a cumulative saturation; and S400: comprehensively characterizing the lower limit of oil accumulation of the deep marine carbonate reservoir according to the first porosity, the first permeability, the second porosity, the second permeability and the lower limit flow pore throat radius for oil accumulation.

In some preferred implementation, the step of collecting the set number of core samples within the set porosity range may include: collecting the set number of core samples within the set porosity range according to a set porosity increasing ratio.

In some preferred implementation, the water-oil displacement NMR experiment may include:

subjecting the collected core samples to drying, vacuuming, and pressurizing and saturation with simulated formation water;

subjecting the core samples to drying, vacuuming, and pressurizing and saturation with simulated oil, after the pressurizing and saturation with simulated formation water; and applying a confining pressure to the core samples after the pressurizing and saturation with simulated oil, displacing the oil with an aqueous solution of manganese at a constant pressure of 20 MPa, and finally obtaining the movable oil ratio of each of the core samples;

where, the drying is carried out for $T_1$, $T_1=24$ h, at $t_1$, $t_1=105°$ C.;

the vacuuming is carried out for $T_2$, $T_2=24$ h, at $P_1$, $P_1<-0.098$ MPa;

the pressurizing and saturation with simulated formation water is carried out for $T_3$, $T_3=48$ h, at $P_2$, $P_2=30$ MPa; and the pressurizing and saturation with simulated oil is carried out with 5 #white oil for $T_4$, $T_4=48$ h, at $P_3$, $P_3=30$ MPa.

In some preferred implementation, the step of determining the lower limit porosity and permeability for oil accumulation based on the boundary line and the movable oil ratio may include:

defining a porosity and a permeability corresponding to the boundary line as the lower limit porosity and permeability for oil accumulation; and defining lower limit porosity and permeability corresponding to a movable oil ratio approaching 0 in each of the core samples as the lower limit porosity and permeability for oil accumulation.

In some preferred implementation, the step of determining the minimum flow pore throat radii corresponding to each of the core samples according to the cumulative permeability contribution may include:

defining flow pore throat radii corresponding to a cumulative permeability contribution of 99.99% as the minimum flow pore throat radii corresponding to each of the core samples.

In some preferred implementation, the cumulative permeability contribution may be calculated as follows:

$$\sum K = \sum \Delta K_i$$
$$\Delta K_i = \frac{\Delta KF_i}{\sum \Delta KF_i} \times 100$$
$$\Delta KF_i = \left(\frac{1}{Pc_i^2} + \frac{1}{Pc_{i+1}^2}\right) \cdot \Delta S_{Hg(i-i+1)}$$

where, $\Sigma K$ denotes the cumulative permeability contribution; $\Delta KF_i$ denotes an interval permeability; $Pc_i$ denotes an interval capillary pressure; $\Delta S_{Hgi}$ denotes an interval mercury injection increment; $\Delta K_i$ denotes an interval permeability contribution, that is, permeability contributions of different flow pore throat radii; and the subscript i is a natural number.

In some preferred implementation, the step of comprehensively characterizing the lower limit of oil accumulation of the deep marine carbonate reservoir according to the first porosity, the first permeability, the second porosity, the second permeability and the lower limit flow pore throat radius for oil accumulation may include:

comprehensively characterizing the lower limit of oil accumulation of the deep marine carbonate reservoir by a smaller one of the first porosity and the second porosity, a smaller one of the first permeability and the second permeability, and the lower limit flow pore throat radius for oil accumulation.

A second aspect of the present invention proposes a system for comprehensively characterizing a lower limit of oil accumulation of a deep marine carbonate reservoir, aiming to predict the lower limit of oil accumulation of the deep marine carbonate reservoir, including: a statistical characterization module, an experimental characterization module, a statistical and experimental characterization module and a comprehensive characterization module, where the statistical characterization module is configured for: acquiring historical data of a deep marine carbonate reservoir to be predicted, such as a burial depth, a porosity, a permeability and a fluid encountered during drilling, where the encountered fluid includes an oil layer and a dry layer; constructing a first cross plot and a second cross plot; obtaining a boundary line between the dry layer and the oil layer; and determining lower limit porosity and permeability for oil accumulation based on the boundary line as a first porosity and a first permeability, respectively, where the first cross plot is a cross plot of the encountered fluid, the burial depth and the porosity; and the second cross plot is a cross plot of the encountered fluid, the burial depth and the permeability;

the experimental characterization module is configured for: collecting a set number of core samples within a set porosity range from the deep marine carbonate reservoir to be predicted, and measuring a porosity, a permeability and an oil saturation of each of the core samples by an NMR instrument; subjecting the core samples to a water-oil displacement NMR experiment; obtaining a movable oil ratio according to a change in the oil saturation of each of the core samples during the water-oil displacement NMR experiment; and determining lower limit porosity and permeability for oil accumulation based on the movable oil ratio as a second porosity and a second permeability, respectively;

the statistical and experimental characterization module is configured for: collecting core samples again from the deep marine carbonate reservoir to be predicted, and performing a mercury injection experiment; calculating, based on parameters acquired by the mercury injection experiment, permeability contributions of different flow pore throat radii by a Purcell formula, and accumulating to obtain a cumulative permeability contribution; determining minimum flow pore throat radii corresponding to each of the core samples according to the cumulative permeability contribution; and determining a smallest one among the minimum flow pore throat radii as a lower limit flow pore throat radius for oil accumulation, where the parameters acquired by the mercury injection experiment include a mercury injection increment, a flow pore throat radius, a J function value and a cumulative saturation; and the comprehensive characterization module is configured for: comprehensively characterizing the lower limit of oil accumulation of the deep marine carbonate reservoir according to the first porosity, the first permeability, the second porosity, the second permeability and the lower limit flow pore throat radius for oil accumulation.

A third aspect of the present invention provides an electronic device, including: at least one processor and a memory communicatively connected to the at least one processor, where the memory stores an instruction executable by the processor; and the instruction is executed by the processor to implement the above method for comprehensively characterizing the lower limit of oil accumulation of the deep marine carbonate reservoir.

The present invention has the following advantages:

The present invention overcomes the problem that the prior art cannot accurately determine the lower limit of oil accumulation of the deep marine carbonate reservoir, and can predict and identify deep effective reservoirs.

The present invention combines statistical analysis and experimental analysis to comprehensively characterize the lower limit of oil accumulation of the deep marine carbonate reservoir through multiple means, so as to predict and identify deep effective reservoirs. The present invention scientifically reveals the prospect of deep oil exploration, evaluates the risk of deep oil exploration, and provides powerful theoretical guidance and technical support for the optimization of favorable exploration targets for the deep marine carbonate reservoir.

BRIEF DESCRIPTION OF THE DRAWINGS

Other features, objectives and advantages of the present invention will become more apparent upon reading the detailed description of the non-restrictive embodiments made below with reference to the drawings.

FIG. 1 is a flowchart of a method for comprehensively characterizing a lower limit of oil accumulation of a deep marine carbonate reservoir according to an embodiment of the present invention;

FIG. 2 is a block diagram of a system for comprehensively characterizing the lower limit of oil accumulation of the deep marine carbonate reservoir according to an embodiment of the present invention;

FIG. 5A shows a cross plot of a movable oil ratio and a porosity of a core sample, and FIG. 5B shows a cross plot of the movable oil ratio and a permeability of the core sample;

DETAILED DESCRIPTION OF THE EMBODIMENTS

Figure 3:
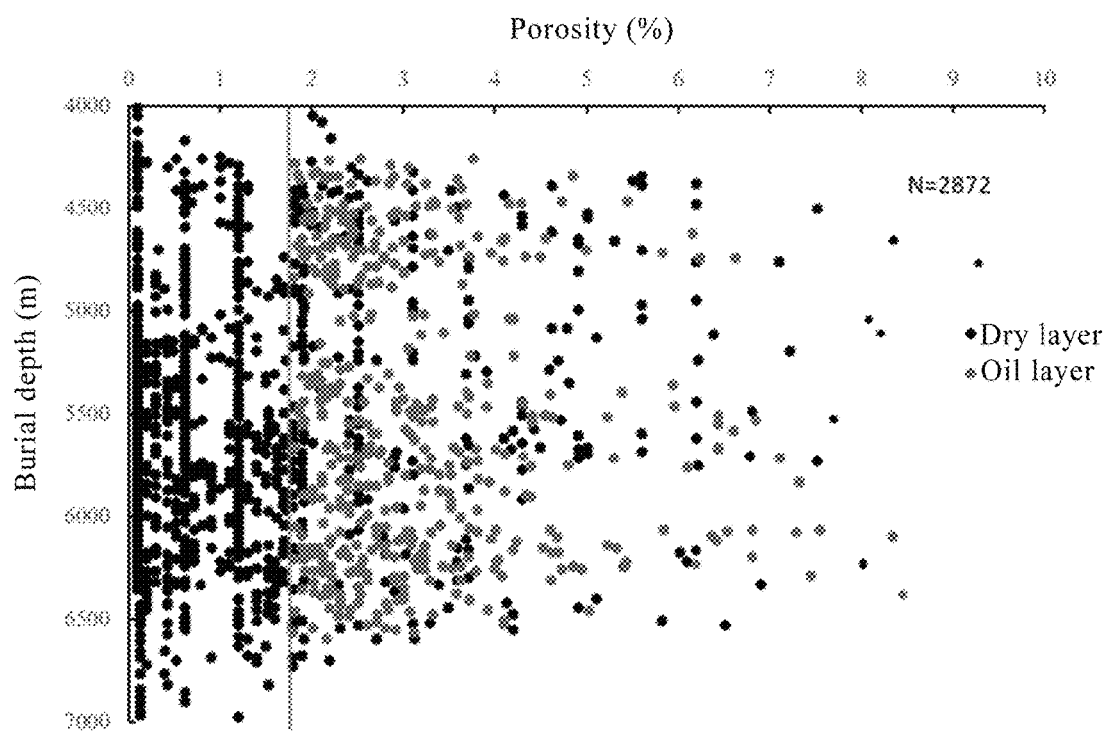
FIG. 3 shows a cross plot of a porosity, a burial depth and an encountered fluid of a Lower Ordovician deep marine carbonate reservoir in the Tazhong area of the Tarim Basin in China according to an embodiment of the present invention.

In order to make the objectives, technical solutions and advantages of the embodiments of the present invention clearer, the technical solutions in the embodiments of the present invention will be clearly and completely described below in conjunction with the drawings in the embodiments of the present invention. Obviously, the described embodiments are some, rather than all of the embodiments of the present invention. All other embodiments obtained by those of ordinary skill in the art based on the embodiments of the present invention without creative efforts should fall within the protection scope of the present invention.

The present invention will be further described in detail below with reference to the drawings and embodiments. It may be understood that the specific embodiments described herein are merely intended to explain the related invention, rather than to limit the present invention. It should be noted that the embodiments in the present invention and features in the embodiments may be combined with each other if no conflict occurs.

A first embodiment of the present invention proposes a method for comprehensively characterizing a lower limit of oil accumulation of a deep marine carbonate reservoir, aiming to predict the lower limit of oil accumulation of the deep marine carbonate reservoir. As shown in FIG. 1, the method includes:

S100: Acquire historical data of a deep marine carbonate reservoir to be predicted, such as a burial depth, a porosity, a permeability and a fluid encountered during drilling, where the encountered fluid includes an oil layer and a dry layer; constructing a first cross plot and a second cross plot; obtain a boundary line between the dry layer and the oil layer; and determine lower limit porosity and permeability for oil accumulation based on the boundary line as a first porosity and a first permeability, respectively, where the first cross plot is a cross plot of the encountered fluid, the burial depth and the porosity; and the second cross plot is a cross plot of the encountered fluid, the burial depth and the permeability.

S200: Collect a set number of core samples within a set porosity range from the deep marine carbonate reservoir to be predicted, and measuring a porosity, a permeability and an oil saturation of each of the core samples by a nuclear magnetic resonance (NMR) instrument; subject the core samples to a water-oil displacement NMR experiment; obtain a movable oil ratio according to a change in the oil saturation of each of the core samples during the water-oil displacement NMR experiment; and determine lower limit porosity and permeability for oil accumulation based on the movable oil ratio as a second porosity and a second permeability, respectively.

S300: Collect core samples again from the deep marine carbonate reservoir to be predicted, and perform a mercury injection experiment; calculate, based on parameters acquired by the mercury injection experiment, permeability contributions of different flow pore throat radii by a Purcell formula, and accumulate to obtain a cumulative permeability contribution; determine minimum flow pore throat radii corresponding to each of the core samples according to the cumulative permeability contribution; and determine a smallest one among the minimum flow pore throat radii as a lower limit flow pore throat radius for oil accumulation, where the parameters acquired by the mercury injection experiment include a mercury injection increment, a flow pore throat radius, a J function value and a cumulative saturation.

S400: Comprehensively characterize a lower limit of oil accumulation of the deep marine carbonate reservoir according to the first porosity, the first permeability, the second porosity, the second permeability and the lower limit flow pore throat radius for oil accumulation.

In order to more clearly describe the method for comprehensively characterizing the lower limit of oil accumulation of the deep marine carbonate reservoir, the steps of an embodiment of the method are described in detail below with reference to the drawings.

The present invention adopts the following technical solution: 1) determine lower limit porosity and permeability for oil accumulation of a deep marine carbonate reservoir by a statistical method; 2) determine lower limit porosity and permeability for oil accumulation of the deep marine carbonate reservoir by an experimental method; 3) determine a lower limit pore throat radius for oil accumulation of the deep marine carbonate reservoir by experimental and statistical methods; and 4) comprehensively characterize the lower limit of oil accumulation of the deep marine carbonate reservoir. The technical solution specifically includes:

S100: Acquire historical data of a deep marine carbonate reservoir to be predicted, such as a burial depth, a porosity, a permeability and a fluid encountered during drilling, where the encountered fluid includes an oil layer and a dry layer; construct a first cross plot and a second cross plot; obtain a boundary line between the dry layer and the oil layer; and determine lower limit porosity and permeability for oil accumulation based on the boundary line as a first porosity and a first permeability, respectively, where the first cross plot is a cross plot of the encountered fluid, the burial depth and the porosity; and the second cross plot is a cross plot of the encountered fluid, the burial depth and the permeability.

In this embodiment, the step of determining the lower limit porosity and permeability for oil accumulation includes:

S110: Collect the data of the deep marine carbonate reservoir to be predicted, such as the burial depth, the porosity, the permeability and the encountered fluid (including an oil layer and a dry layer); construct a cross plot of the encountered fluid, the burial depth and the porosity and a cross plot of the encountered fluid, the burial depth and the permeability; and take the cross plot of the encountered fluid, the burial depth and the porosity as a first cross plot and the cross plot of the encountered fluid, the burial depth and the permeability as a second cross plot.

S120: Obtain a boundary line between the dry layer and the oil layer. On the cross plot of the encountered fluid, the burial depth and the porosity, the dry layer is on a side with a smaller porosity, and the oil layer is on a side with a greater porosity. That is, the side smaller than the boundary line is a completely dry layer, and the side greater than the boundary line begins to appear as an oil layer. Below the lower limit porosity, oil cannot enter the reservoir to accumulate, and the porosity corresponding to the boundary line is the lower limit porosity for oil accumulation. In the same way, the lower limit permeability for oil accumulation is obtained.

The Tarim Basin is the largest petroliferous basin in China. It is located in Xinjiang, China, and has an area of about $56 \times 10^4$ m$^2$. The Tarim Basin is rich in oil and gas and is the most important oil and gas supply area in China. The proven oil and gas reserves of the basin are $35.6 \times 10^8$ t oil equivalent, and the prospective resources are $114 \times 10^8$ t, ranking third among the national petroliferous basins. The strata below the Silurian in the Tarim Basin are marine carbonate deposits, and the Lower Ordovician of the target layer is the main oil and gas storage and production layer. In the Tazhong area of the Basin, the Lower Ordovician carbonate rocks are found at burial depths of 3,356 m and 6,744 m.

Figure 4:
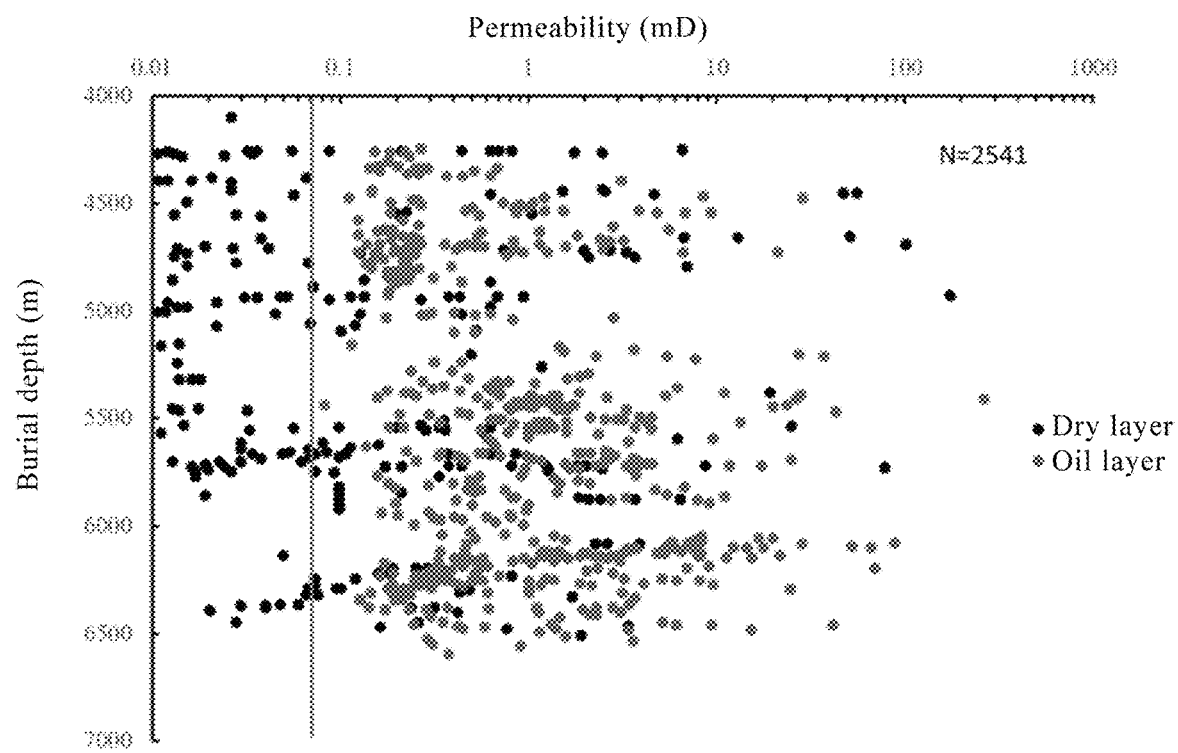
FIG. 4 shows a cross plot of a permeability, a burial depth and an encountered fluid of the Lower Ordovician deep marine carbonate reservoir in the Tazhong area of the Tarim Basin in China according to an embodiment of the present invention.

The present invention is based on the production practice of Tarim Oilfield, data of the effective carbonate reservoirs of the Lower Ordovician Yingshan Formation, the collected porosity and permeability data of the Lower Ordovician carbonate reservoirs and the logging interpretations of oil and dry layers. When the porosity of the reservoir is less than 1.8%, the layer encountered is a completely dry layer, and when the porosity of the reservoir is greater than 1.8%, an oil layer begins to appear. On the depth profile, according to the porosity of the reservoir and the interpretation results of the oil and dry layers, almost 100% of the oil layer is located to the right of the boundary line (a line with a porosity of 1.8%), and 70% of the dry layer is located to the left of the boundary line (as shown in FIG. 3). When the permeability of the reservoir is lower than 0.07 mD, the layer encountered is a completely dry layer, and when the porosity of the reservoir is greater than 0.07 mD, an oil layer begins to appear (as shown in FIG. 4). For the convenience of research, in the application of this embodiment, it is considered that 1 µm$^2$ is equal to $10^3$ mD. On the depth profile, according to the permeability of the reservoir and the interpretation results of oil and dry layers, almost 100% of the oil layer is located to the right of the boundary line (a line with a permeability of 0.07 mD), and 51% of the dry layer is located to the left of the boundary line. Based on this, it is determined that the lower limit porosity and permeability of Lower Ordovician deep marine carbonate reservoir in the Tazhong area are 1.8% and 0.07 mD, respectively.

S200: Collect a set number of core samples within a set porosity range from the deep marine carbonate reservoir to be predicted, and measure a porosity, a permeability and an oil saturation of each of the core samples by an NMR instrument; subject the core samples to a water-oil displacement NMR experiment; obtain a movable oil ratio according to a change in the oil saturation of each of the core samples during the water-oil displacement NMR experiment; and determine lower limit porosity and permeability for oil accumulation based on the movable oil ratio as a second porosity and a second permeability, respectively.

In this embodiment, the NMR technology and the water-oil displacement experiment are combined to visually display the size and distribution of movable oil in different flow pore throat radius intervals, monitor the entire process of water-oil displacement, measure the change of NMR signal online, and monitor the change of the movable oil ratio in the whole process. Lower limit porosity and permeability corresponding to a movable oil ratio approaching 0 of the core samples are defined as the lower limit porosity and permeability for oil accumulation. This step specifically includes:

S210: Collect 10 core samples from the deep marine carbonate reservoir to be predicted, and collect ultra-tight, tight and high-porosity samples according to an interpretation result from a neutron logging curve, etc., that is, collect a set number of core samples within a set porosity range.

The step of collecting the set number of core samples within the set porosity range includes: collecting the set number of core samples within the set porosity range according to a set porosity increasing ratio.

In this embodiment, preferably, the porosity of the core samples is distributed between 0.2% and 10%, and is specifically <0.2%, 0.5%, 1%, 1.5%, 2%, 2.5%, 3%, 5%, 7.5%, 10%, etc.

S220: Perform a three-step experiment. First, the porosity, permeability and oil saturation of the 10 core samples are accurately measured by an NMR instrument, and the relevant data are recorded. Constant oil saturation means that the corresponding movable oil ratio is 0. The porosity and permeability corresponding to the movable oil ratio of 0 are the lower limit of oil accumulation of the reservoir. That is, the movable oil ratio is obtained according to the change of the oil saturation of the core sample in the NMR experiment during the water-oil displacement process, and the lower limit porosity and permeability are determined. Secondly, an NMR experiment is carried out during the water-oil displacement process, and the movable oil ratio in each core during this process is measured. The conditions and process of the NMR experiment in the water-oil displacement process are as follows. (1) Perform drying, vacuuming, pressurizing and saturation with simulated formation water, etc. (2) Measure and output an NMR signal in the state of saturated formation water (used to calculate water saturation). (3) Carry out drying, vacuuming, pressurizing and saturation with simulated oil, etc. (4) Apply a confining pressure to displace oil with manganese-containing water at a constant displacement pressure of 20 MPa, and measure and output an NMR signal. (5) An online water-oil displacement NMR system determines and records the movable oil ratio of the 10 cores containing simulated oil (i.e., core samples injected with white oil) based on the two NMR signals. Finally, graphs are drawn and interpretation results are obtained. The drying is carried out for $T_1$, $T_1$=24 h, at $t_1$, $t_i$=105° C. The vacuuming is carried out for $T_2$, $T_2$=24 h, at $P_1$, $P_1$<−0.098 MPa. The pressurizing and saturation with simulated formation water is carried out for $T_3$, $T_3$=48 h, at $P_2$, $P_2$=30 MPa. The pressurizing and saturation with simulated oil is carried out with 5 #white oil for $T_4$, $T_4$=48 h, at $P_3$, $P_3$=30 MPa.

Figure 5A:
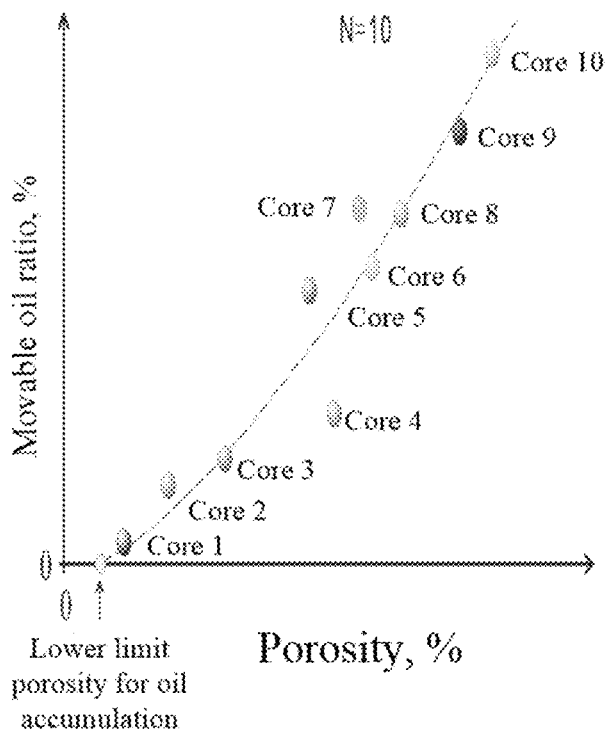
FIGS. 5A-5B show an expected result of online NMR measurement of water-oil displacement and determination of a lower limit of oil accumulation of the deep marine carbonate reservoir according to an embodiment of the present invention, where
Figure 5B:
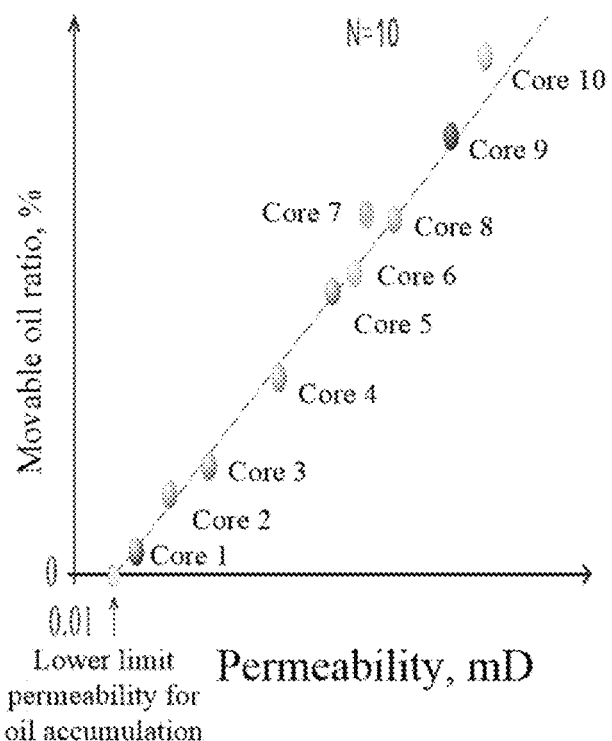

S230: Obtain the porosity, permeability and movable oil ratio of the 10 core samples according to the NMR experiment of the water-oil displacement process, and construct a cross plot of the porosity and movable oil ratio and a cross plot of the permeability and movable oil ratio, where on the cross plot, the porosity and permeability corresponding to the movable oil ratio approaching 0 are the lower limit porosity and permeability (as shown in FIGS. 5A-5B).

S300: Collect core samples again from the deep marine carbonate reservoir to be predicted, and perform a mercury injection experiment; calculate, based on parameters acquired by the mercury injection experiment, permeability contributions of different flow pore throat radii by a Purcell formula, and accumulate to obtain a cumulative permeability contribution; determine minimum flow pore throat radii corresponding to each of the core samples according to the cumulative permeability contribution; and determine a smallest one among the minimum flow pore throat radii as a lower limit flow pore throat radius for oil accumulation, where the parameters acquired by the mercury injection experiment include a mercury injection increment, a flow pore throat radius, a J function value and a cumulative saturation.

The step of determining the lower limit pore throat radius of the deep marine carbonate reservoir by experimental and statistical methods specifically includes:

S310: Subject the collected core samples of the deep marine carbonate reservoir to be predicted to a common mercury injection experiment.

S320: Calculate, based on parameters acquired by the mercury injection experiment, a permeability contribution of different flow pore throat radii to the permeability by a Purcell formula (a formula designed to calculate a cumulative permeability contribution of a sample to permeability), and accumulate the permeability contribution to obtain a cumulative permeability contribution of 99.99%; and determine minimum flow pore throat radii corresponding to the core samples.

The cumulative permeability contribution is calculated as follows:

$$\Delta KF_i = \left(\frac{1}{Pc_{i^2}} + \frac{1}{Pc_{i+1^2}}\right) \cdot \Delta S_{Hg(i-i+1)}$$

$$\Delta K_i = \frac{\Delta KF_i}{\sum \Delta KF_i} \times 100$$

$$\sum K = \sum \Delta K_i$$

where, $\Sigma K$ denotes the cumulative permeability contribution; $\Delta KF_i$ denotes an interval permeability; $Pc_i$ denotes an interval capillary pressure; $\Delta S_{Hgi}$ denotes an interval mercury injection increment; $\Delta K_i$ denotes an interval permeability contribution, that is, permeability contributions of different flow pore throat radii; and the subscript i is a natural number.

Figure 6:
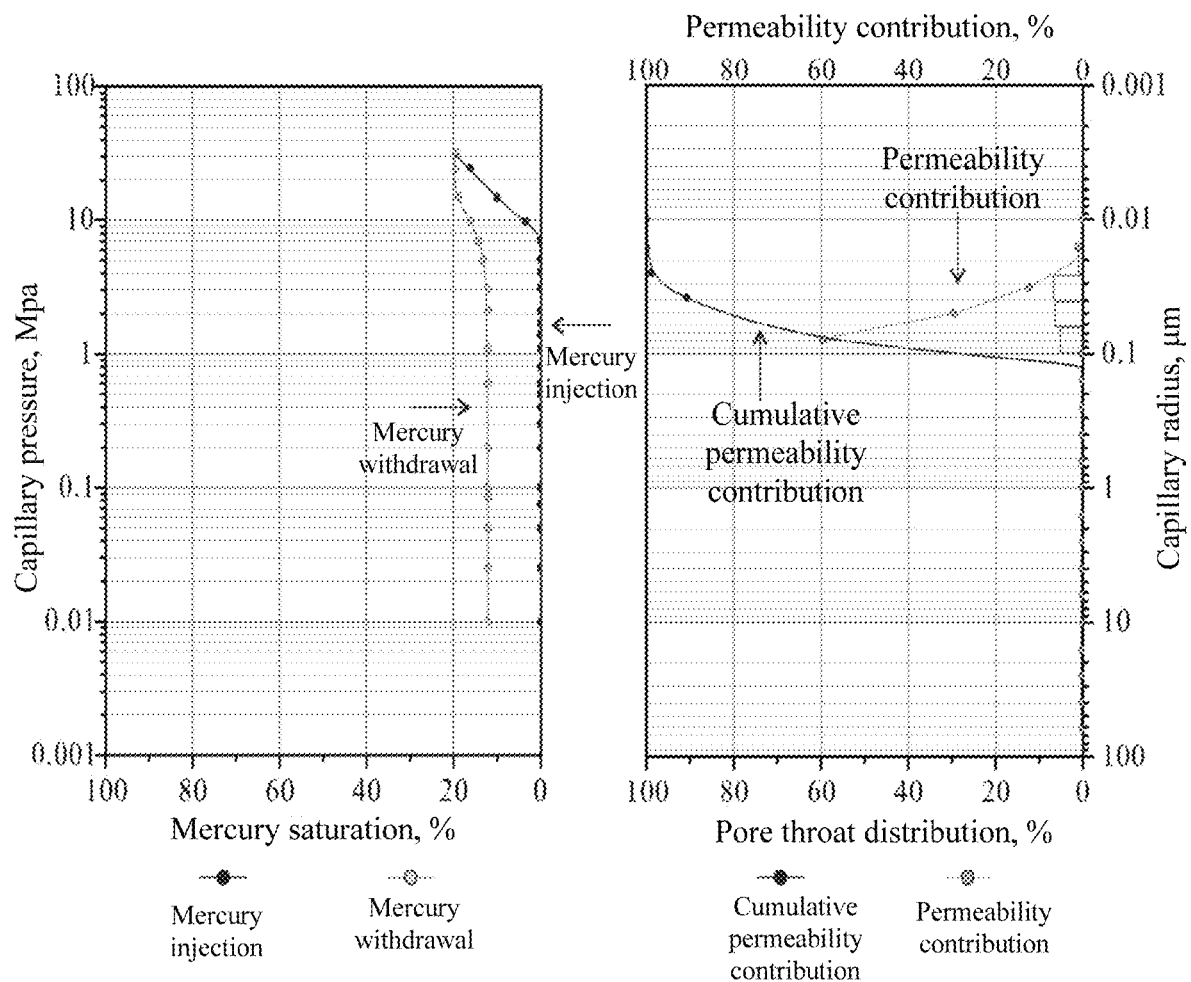
FIG. 6 shows a mercury injection test curve and a pore throat distribution of a core sample of a Lower Ordovician carbonate oil layer in Tazhong 85 Well in the Tarim Basin in China according to an embodiment of the present invention.

355 deep marine carbonate cores of the Lower Ordovician in the Tazhong area of the Tarim Basin are subjected to a mercury injection experiment, and mercury injection capillary curves and pore throat distributions are obtained. The mercury injection capillary curve and pore throat distribution of the core at 4,632.05 m of the Lower Ordovician carbonate rock (gray limestone) in Well Tazhong 58 in the Tazhong area are shown in FIG. 6.

Figure 7:
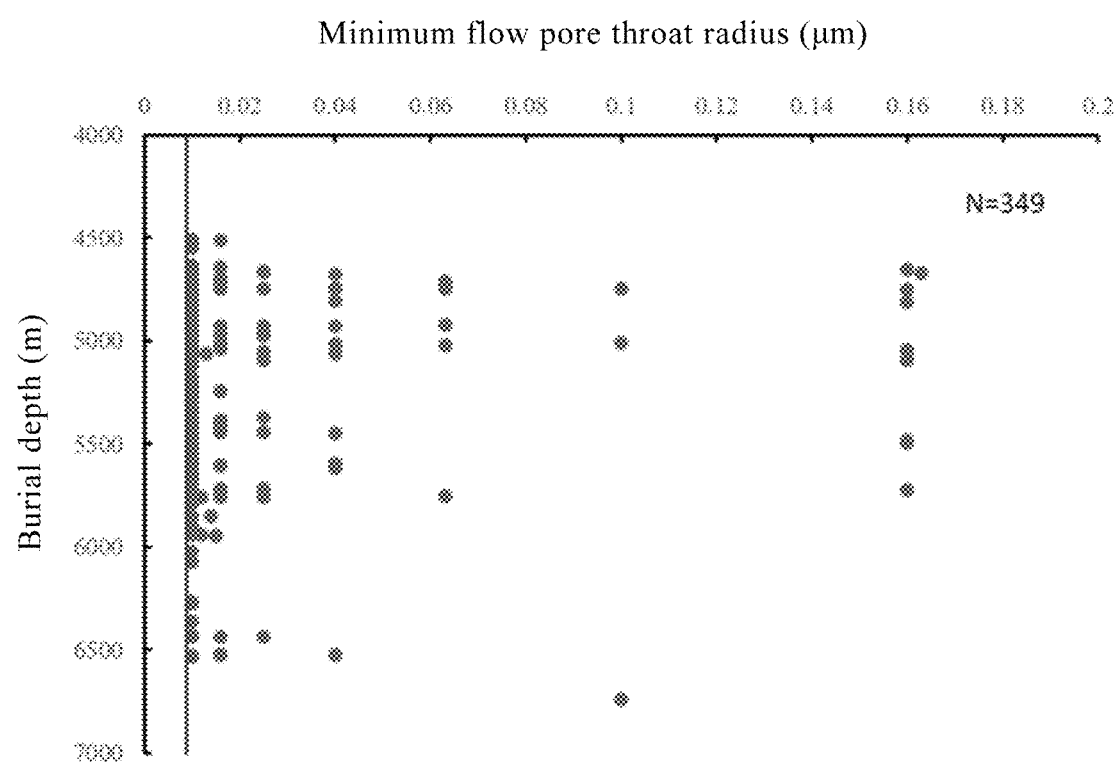
FIG. 7 shows a lower limit pore throat radius for oil accumulation of the Lower Ordovician carbonate reservoir in the Tazhong area of the Tarim Basin in China according to an embodiment of the present invention.

Substituting the mercury injection data acquired from the experiment into the Purcell formula, the pore throat radius corresponding to the cumulative permeability contribution of 99.99% is the minimum flow pore throat radius. The minimum flow pore throat radius of the Lower Ordovician carbonate reservoir in Well Tazhong 58 in the Tazhong area of the Tarim Basin is 0.012 μm. Other 335 Lower Ordovician limestone samples are subjected to a mercury injection experiment to obtain the minimum flow pore throat radius. The minimum value of the minimum flow pore throat radius of all samples is calculated to be 0.01 μm (as shown in FIG. 7), which is the lower limit pore throat radius of the Lower Ordovician deep marine carbonate reservoir in the Tazhong area.

S330: Calculate a minimum value among the minimum flow pore throat radii of all the core samples as a lower limit flow pore throat radius of the deep marine carbonate reservoir.

S400: Comprehensively characterize a lower limit of oil accumulation of the deep marine carbonate reservoir according to the first porosity, the first permeability, the second porosity, the second permeability and the lower limit flow pore throat radius for oil accumulation.

In this embodiment, the step of comprehensive characterizing the lower limit of oil accumulation of the deep marine carbonate reservoir according to the lower limit porosity, permeability and pore throat radius determined by the above steps specifically includes:

Comprehensively characterize the lower limit of oil accumulation of the deep marine carbonate reservoir by a smaller one of the first porosity and the second porosity, a smaller one of the first permeability and the second permeability, and the lower limit flow pore throat radius for oil accumulation.

For the 355 deep marine carbonate cores of the Lower Ordovician in the Tazhong area of the Tarim Basin, the lower limit of oil accumulation of the deep marine carbonate reservoir in the Tazhong area of the Tarim Basin is determined as shown in Table 1. The lower limit of oil accumulation of the Lower Ordovician deep marine carbonate reservoir in the Tazhong area of the Tarim Basin is comprehensively determined, including a porosity of 1.8%, a permeability of 0.07 mD and a pore throat radius of 0.01 μm.

TABLE 1

| Indicator | Value | Determination method |
| --- | --- | --- |
| Porosity | 1.8% | Statistical method |
| Permeability | 0.07 mD | Statistical method |
| Porosity | — | Experimental method |
| Permeability | — | Experimental method |
| Pore throat radius | 0.01 μm | Statistical + Experimental method |

A second embodiment of the present invention proposes a system for comprehensively characterizing a lower limit of oil accumulation of a deep marine carbonate reservoir, aiming to predict the lower limit of oil accumulation of the deep marine carbonate reservoir. As shown in FIG. 2, the system includes: a statistical characterization module 100, an experimental characterization module 200, a statistical and experimental characterization module 300 and a comprehensive characterization module 400.

The statistical characterization module 100 is configured for: acquiring historical data of a deep marine carbonate reservoir to be predicted, such as a burial depth, a porosity, a permeability and a fluid encountered during drilling, where the encountered fluid includes an oil layer and a dry layer; constructing a first cross plot and a second cross plot; obtaining a boundary line between the dry layer and the oil layer; and determining lower limit porosity and permeability for oil accumulation based on the boundary line as a first porosity and a first permeability, respectively, where the first cross plot is a cross plot of the encountered fluid, the burial depth and the porosity; and the second cross plot is a cross plot of the encountered fluid, the burial depth and the permeability.

The experimental characterization module 200 is configured for: collecting a set number of core samples within a set porosity range from the deep marine carbonate reservoir to be predicted, and measuring a porosity, a permeability and an oil saturation of each of the core samples by an NMR instrument; subjecting the core samples to a water-oil displacement NMR experiment; obtaining a movable oil ratio according to a change in the oil saturation of each of the core samples during the water-oil displacement NMR experiment; and determining lower limit porosity and permeability for oil accumulation based on the movable oil ratio as a second porosity and a second permeability, respectively.

The statistical and experimental characterization module 300 is configured for: collecting core samples again from the deep marine carbonate reservoir to be predicted, and performing a mercury injection experiment; calculating, based on parameters acquired by the mercury injection experiment, permeability contributions of different flow pore throat radii by a Purcell formula, and accumulating to obtain a cumulative permeability contribution; determining minimum flow pore throat radii corresponding to each of the core samples according to the cumulative permeability contribution; and determining a smallest one among the minimum flow pore throat radii as a lower limit flow pore throat radius for oil accumulation, where the parameters acquired by the mercury injection experiment include a mercury injection increment, a flow pore throat radius, a J function value and a cumulative saturation.

The comprehensive characterization module 400 is configured for: comprehensively characterizing the lower limit of oil accumulation of the deep marine carbonate reservoir according to the first porosity, the first permeability, the second porosity, the second permeability and the lower limit flow pore throat radius for oil accumulation.

Those skilled in the art can clearly understand that, for convenience and brevity of description, reference can be made to corresponding processes in the foregoing method embodiments for a specific working process and a related description of the above-described system. Details are not described herein again.

It should be noted that the system for comprehensively characterizing the lower limit of oil accumulation of the deep marine carbonate reservoir provided by the above embodiment is only described by taking the division of the above functional modules as an example. In practical applications, the above functions can be completed by different functional modules as required, that is, the modules or steps in the embodiments of the present invention are further decomposed or combined. For example, the modules of the above embodiments may be combined into one module, or may be further divided into multiple sub-modules to complete all or part of the functions described above. The names of the modules and steps involved in the embodiments of the present invention are only for distinguishing each module or step, and should not be regarded as improper limitations on the present invention.

A third embodiment of the present invention provides a device for comprehensively characterizing a lower limit of oil accumulation of a deep marine carbonate reservoir. The device includes an exploration device, a signal acquisition device and a central processing device.

The exploration device includes a drilling rig, and is configured for collecting a set number of core samples within a set porosity range from the deep marine carbonate reservoir to be predicted.

The signal acquisition device is configured for acquiring NMR signals under a first state and a second state in a water-oil displacement NMR experiment, where the first state is defined by a pressurizing and saturation with simulated formation water, and the second state is defined by manganese-containing water flooding at a confining pressure and a displacement pressure of 20 MPa.

The central processing device includes a graphics processing unit (GPU), and is configured for: acquiring historical data of a deep marine carbonate reservoir to be predicted, such as a burial depth, a porosity, a permeability and a fluid encountered during drilling, where the encountered fluid includes an oil layer and a dry layer; constructing a first cross plot and a second cross plot; obtaining a boundary line between the dry layer and the oil layer; and determining lower limit porosity and permeability for oil accumulation based on the boundary line as a first porosity and a first permeability, respectively, where the first cross plot is a cross plot of the encountered fluid, the burial depth and the porosity; and the second cross plot is a cross plot of the encountered fluid, the burial depth and the permeability;

measuring a porosity, a permeability and an oil saturation of each of the core samples by an NMR instrument; subjecting the core samples to a water-oil displacement NMR experiment; obtaining a movable oil ratio according to a change in the oil saturation of each of the core samples during the water-oil displacement NMR experiment; and determining lower limit porosity and permeability for oil accumulation based on the movable oil ratio as a second porosity and a second permeability, respectively;

calculating, based on parameters acquired by the mercury injection experiment, permeability contributions of different flow pore throat radii by a Purcell formula, and accumulating to obtain a cumulative permeability contribution; determining minimum flow pore throat radii corresponding to each of the core samples according to the cumulative permeability contribution; and determining a smallest one among the minimum flow pore throat radii as a lower limit flow pore throat radius for oil accumulation, where the parameters acquired by the mercury injection experiment include a mercury injection increment, a flow pore throat radius, a J function value and a cumulative saturation; and comprehensively characterizing the lower limit of oil accumulation of the deep marine carbonate reservoir according to the first porosity, the first permeability, the second porosity, the second permeability and the lower limit flow pore throat radius for oil accumulation.

A fourth embodiment of the present invention provides an electronic device, including at least one processor and a memory communicatively connected to the at least one processor, where the memory stores an instruction executable by the processor; and the instruction is executed by the processor to implement the above method for comprehensively characterizing a lower limit of oil accumulation of a deep marine carbonate reservoir.

Those skilled in the art can clearly understand that, for convenience and brevity of description, reference can be made to a corresponding process in the above method embodiment for specific working processes and related descriptions of the above device for comprehensively characterizing the lower limit of oil accumulation of the deep marine carbonate reservoir and electronic device. Details are not described herein again.

Those skilled in the art should be aware that the modules and method steps of the embodiments described in the embodiments disclosed herein may be implemented by electronic hardware, computer software or a combination thereof. The programs corresponding to software modules and method steps may be placed in random access memory (RAM), internal memory, read-only memory (ROM), electrically programmable ROM, electrically erasable programmable (ROM), registers, hard disk, removable disk, compact disc read-only memory (CD-ROM), or in any other form of storage medium known in the technical field. In order to clearly illustrate the interchangeability of THE electronic hardware and software, the composition and steps of each embodiment are generally described in accordance with the function in the above description. Whether the functions are carried out by electronic hardware or software depends on particular applications and design constraints of the technical solutions. Those skilled in the art may use different methods to implement the described functions for each specific application, but such implementation should not be considered to be beyond the scope of the present invention.

Terms "include", "comprise" or any other variations thereof are intended to cover non-exclusive inclusions, so that a process, a method, an article, or a device/apparatus including a series of elements not only includes those elements, but also includes other elements that are not explicitly listed, or also includes inherent elements of the process, the method, the article or the device/apparatus.

The technical solutions of the present invention are described with reference to the preferred implementations and drawings. Those skilled in the art should easily understand that the protection scope of the present invention is apparently not limited to these specific implementations. Those skilled in the art can make equivalent changes or substitutions to the relevant technical features without departing from the principles of the present invention, and the technical solutions after these changes or substitutions should fall within the protection scope of the present invention.

What is claimed is:

1. A method for characterizing a lower limit of oil accumulation of a deep marine carbonate reservoir, aiming to predict the lower limit of oil accumulation of the deep marine carbonate reservoir, comprising the following steps:

S100: acquiring historical data of a deep marine carbonate reservoir to be predicted, the historical data comprising a burial depth, a porosity, a permeability and a fluid encountered during drilling, wherein the encountered fluid comprises an oil layer and a dry layer; constructing a first cross plot and a second cross plot; obtaining a boundary line between the dry layer and the oil layer; and determining lower limit porosity and permeability for oil accumulation based on the boundary line as a first porosity and a first permeability, respectively, wherein the first cross plot is a cross plot of the encountered fluid, the burial depth and the porosity; and the second cross plot is a cross plot of the encountered fluid, the burial depth and the permeability;

S200: collecting a set number of core samples within a set porosity range from the deep marine carbonate reservoir to be predicted, and measuring a porosity, a permeability and an oil saturation of each of the core samples by a nuclear magnetic resonance (NMR) instrument; subjecting the core samples to a water-oil displacement NMR experiment; obtaining a movable oil ratio according to a change in the oil saturation of each of the core samples during the water-oil displacement NMR experiment; and determining lower limit porosity and permeability for oil accumulation based on the movable oil ratio as a second porosity and a second permeability, respectively;

S300: collecting core samples again from the deep marine carbonate reservoir to be predicted, and performing a mercury injection experiment; calculating, based on parameters acquired by the mercury injection experiment, permeability contributions of different flow pore throat radii by a Purcell formula, and accumulating the permeability contributions to obtain a cumulative permeability contribution; determining minimum flow pore throat radii corresponding to each of the core samples according to the cumulative permeability contribution; and determining a smallest one among the minimum flow pore throat radii as a lower limit flow pore throat radius for oil accumulation, wherein the parameters acquired by the mercury injection experiment comprise a mercury injection increment, a flow pore throat radius, a J function value and a cumulative saturation;

wherein, the water-oil displacement NMR experiment comprises:

subjecting the collected core samples to drying, vacuuming, and pressurizing and saturation with simulated formation water;

subjecting the core samples to drying, vacuuming, and pressurizing and saturation with simulated oil, after the pressurizing and saturation with simulated formation water; and applying a confining pressure to the core samples after the pressurizing and saturation with simulated oil, displacing the oil with an aqueous solution of manganese at a constant pressure of 20 MPa, and finally obtaining the movable oil ratio of each of the core samples;

wherein, the drying is carried out for $T_1$, $T_1=24$ h, at $t_1$, $t_1=105°$ C.;

the vacuuming is carried out for $T_2$, $T_2=24$ h, at $P_1$, $P_1<-0.098$ Mpa;

the pressurizing and saturation with simulated formation water is carried out for $T_3$, $T_3=48$ h, at $P_2$, $P_2=30$ Mpa; and the pressurizing and saturation with simulated oil is carried out with 5 #white oil for $T_4$, $T_4=48$ h, at $P_3$, $P_3=30$ Mpa; and S400: characterizing the lower limit of oil accumulation of the deep marine carbonate reservoir according to the first porosity, the first permeability, the second porosity, the second permeability and the lower limit flow pore throat radius for oil accumulation.

2. The method for characterizing the lower limit of oil accumulation of the deep marine carbonate reservoir according to claim 1, wherein the step of collecting the set number of core samples within the set porosity range comprises: collecting the set number of core samples within the set porosity range according to a set porosity increasing ratio.

3. The method for characterizing the lower limit of oil accumulation of the deep marine carbonate reservoir according to claim 2, wherein the step of determining the lower limit porosity and permeability for oil accumulation based on the boundary line and the movable oil ratio comprises:
 defining a porosity and a permeability corresponding to the boundary line as the lower limit porosity and permeability for oil accumulation; and
 defining lower limit porosity and permeability corresponding to a movable oil ratio approaching 0 in each of the core samples as the lower limit porosity and permeability for oil accumulation.

4. The method for characterizing the lower limit of oil accumulation of the deep marine carbonate reservoir according to claim 1, wherein the step of determining the minimum flow pore throat radii corresponding to each of the core samples according to the cumulative permeability contribution comprises:
 defining flow pore throat radii corresponding to a cumulative permeability contribution of 99.99% as the minimum flow pore throat radii corresponding to each of the core samples.

5. The method for characterizing the lower limit of oil accumulation of the deep marine carbonate reservoir according to claim 4, wherein the cumulative permeability contribution is calculated as follows:

$$\Sigma K = \Sigma \Delta k_i$$

$$\sum K = \sum \Delta K_i$$

$$\Delta K_i = \frac{\Delta KF_i}{\sum \Delta KF_i} \times 100$$

$$\Delta KF_i = \left(\frac{1}{Pc_{i^2}} + \frac{1}{Pc_{i+1^2}}\right) \cdot \Delta S_{Hg(i-i+1)}$$

wherein, $\Sigma K$ denotes the cumulative permeability contribution; $\Delta KF_i$ denotes an interval permeability; $Pc_i$ denotes an interval capillary pressure; $\Delta S_{Hgi}$ denotes an interval mercury injection increment; $\Delta K_i$ denotes an interval permeability contribution, that is, permeability contributions of different flow pore throat radii; and the subscript i is a natural number.

6. The method for characterizing the lower limit of oil accumulation of the deep marine carbonate reservoir according to claim 1, wherein the step of characterizing the lower limit of oil accumulation of the deep marine carbonate reservoir according to the first porosity, the first permeability, the second porosity, the second permeability and the lower limit flow pore throat radius for oil accumulation comprises:
 characterizing the lower limit of oil accumulation of the deep marine carbonate reservoir by a smaller one of the first porosity and the second porosity, a smaller one of the first permeability and the second permeability, and the lower limit flow pore throat radius for oil accumulation.

7. An electronic device, comprising:
 at least one processor and a memory communicatively connected to the at least one processor, wherein
 the memory stores an instruction executable by the processor; and the instruction is executed by the at least one processor to implement the method for characterizing the lower limit of oil accumulation of the deep marine carbonate reservoir according to claim 1.

8. The electronic device according to claim 7, wherein the step of collecting the set number of core samples within the set porosity range comprises: collecting the set number of core samples within the set porosity range according to a set porosity increasing ratio.

9. The electronic device according to claim 8, wherein the step of determining the lower limit porosity and permeability for oil accumulation based on the boundary line and the movable oil ratio comprises:
 defining a porosity and a permeability corresponding to the boundary line as the lower limit porosity and permeability for oil accumulation; and
 defining lower limit porosity and permeability corresponding to a movable oil ratio approaching 0 in each of the core samples as the lower limit porosity and permeability for oil accumulation.

10. The electronic device according to claim 7, wherein the step of determining the minimum flow pore throat radii corresponding to each of the core samples according to the cumulative permeability contribution comprises:
 defining flow pore throat radii corresponding to a cumulative permeability contribution of 99.99% as the minimum flow pore throat radii corresponding to each of the core samples.

11. The electronic device according to claim 10, wherein the cumulative permeability contribution is calculated as follows:

$$\sum K = \sum \Delta K_i$$

$$\Delta K_i = \frac{\Delta KF_i}{\sum \Delta KF_i} \times 100$$

$$\Delta KF_i = \left(\frac{1}{Pc_{i^2}} + \frac{1}{Pc_{i+1^2}}\right) \cdot \Delta S_{Hg(i-i+1)}$$

wherein, $\Sigma K$ denotes the cumulative permeability contribution; $\Delta KF_i$ denotes an interval permeability; $Pc_i$ denotes an interval capillary pressure; $\Delta S_{Hgi}$ denotes an interval mercury injection increment; $\Delta K_i$ denotes an interval permeability contribution, that is, permeability contributions of different flow pore throat radii; and the subscript i is a natural number.

12. The electronic device according to claim 7, wherein the step of characterizing the lower limit of oil accumulation of the deep marine carbonate reservoir according to the first porosity, the first permeability, the second porosity, the second permeability and the lower limit flow pore throat radius for oil accumulation comprises:
 characterizing the lower limit of oil accumulation of the deep marine carbonate reservoir by a smaller one of the first porosity and the second porosity, a smaller one of the first permeability and the second permeability, and the lower limit flow pore throat radius for oil accumulation.

13. A computer system for characterizing the lower limit of oil accumulation of a deep marine carbonate reservoir, aiming to predict the lower limit of oil accumulation of the deep marine carbonate reservoir, comprising: a statistical characterization module, an experimental characterization module, a statistical and experimental characterization module and a characterization module, wherein the statistical characterization module is configured for: acquiring historical data of a deep marine carbonate reservoir to be predicted, the historical data comprising a burial depth, a porosity, a permeability and a fluid encountered during drilling, wherein the encountered fluid comprises an oil layer and a dry layer; constructing a first cross plot and a second cross plot; obtaining a boundary line between the dry layer and the oil layer; and determining lower limit porosity and permeability for oil accumulation based on the boundary line as a first porosity and a first permeability, respectively, wherein the first cross plot is a cross plot of the encountered fluid, the burial depth and the porosity; and the second cross plot is a cross plot of the encountered fluid, the burial depth and the permeability;

the experimental characterization module is configured for: collecting a set number of core samples within a set porosity range from the deep marine carbonate reservoir to be predicted, and measuring a porosity, a permeability and an oil saturation of each of the core samples by an NMR instrument; subjecting the core samples to a water-oil displacement NMR experiment; obtaining a movable oil ratio according to a change in the oil saturation of each of the core samples during the water-oil displacement NMR experiment; and determining lower limit porosity and permeability for oil accumulation based on the movable oil ratio as a second porosity and a second permeability, respectively;

the statistical and experimental characterization module is configured for: collecting core samples again from the deep marine carbonate reservoir to be predicted, and performing a mercury injection experiment; calculating, based on parameters acquired by the mercury injection experiment, permeability contributions of different flow pore throat radii by a Purcell formula, and accumulating the permeability contributions to obtain a cumulative permeability contribution; determining minimum flow pore throat radii corresponding to each of the core samples according to the cumulative permeability contribution; and determining a smallest one among the minimum flow pore throat radii as a lower limit flow pore throat radius for oil accumulation, wherein the parameters acquired by the mercury injection experiment comprise a mercury injection increment, a flow pore throat radius, a J function value and a cumulative saturation;

wherein, the water-oil displacement NMR experiment comprises:

subjecting the collected core samples to drying, vacuuming, and pressurizing and saturation with simulated formation water;

subjecting the core samples to drying, vacuuming, and pressurizing and saturation with simulated oil, after the pressurizing and saturation with simulated formation water; and applying a confining pressure to the core samples after the pressurizing and saturation with simulated oil, displacing the oil with an aqueous solution of manganese at a constant pressure of 20 Mpa, and finally obtaining the movable oil ratio of each of the core samples;

wherein, the drying is carried out for $T_1$, $T_1=24$ h, at $t_1$, $t_1=105°$ C.;

the vacuuming is carried out for $T_2$, $T_2=24$ h, at $P_1$, $P_1<-0.098$ Mpa;

the pressurizing and saturation with simulated formation water is carried out for $T_3$, $T_3=48$ h, at $P_2$, $P_2=30$ Mpa; and the pressurizing and saturation with simulated oil is carried out with 5 #white oil for $T_4$, $T_4=48$ h, at $P_3$, $P_3=30$ Mpa; and the characterization module is configured for: characterizing the lower limit of oil accumulation of the deep marine carbonate reservoir according to the first porosity, the first permeability, the second porosity, the second permeability and the lower limit flow pore throat radius for oil accumulation.

\* \* \* \* \*